United States Patent [19]

Brown et al.

[11] Patent Number: 5,741,713
[45] Date of Patent: Apr. 21, 1998

[54] COMBINATORIAL LIBRARIES OF LABELED BIOCHEMICAL COMPOUNDS AND METHODS FOR PRODUCING SAME

[75] Inventors: Jonathan M. Brown, Baltimore; F.C. Thomas Allnutt, Port Deposit; Hao Chen, Adelphi; Richard Radmer, Clarksville, all of Md.

[73] Assignee: Martek Biosciences Corporation, Columbia, Md.

[21] Appl. No.: 667,723

[22] Filed: Jun. 21, 1996

Related U.S. Application Data

[62] Division of Ser. No. 493,300, Jun. 21, 1995.

[51] Int. Cl.⁶ .......................... G01N 33/543; C12N 1/12; C07K 1/00
[52] U.S. Cl. .......................... 436/518; 436/501; 436/524; 436/528; 436/531; 435/257.1; 530/350; 530/387.1
[58] Field of Search ...................... 436/518, 501, 436/524, 528, 531; 435/7.1, 257.1, 18, 23; 530/350, 357.1

[56] References Cited

U.S. PATENT DOCUMENTS

| | | | |
|---|---|---|---|
| 5,324,658 | 6/1994 | Cox et al. | 435/23 |
| 5,510,240 | 4/1996 | Lam et al. | 435/7.1 |

FOREIGN PATENT DOCUMENTS 94 08051   4/1994   WIPO.

OTHER PUBLICATIONS

Hongatao Yu et al Cell, vol. 76, 933–945 Mar. 11, 1994.
D.M. LeMaster et al., "Preparative-Scale Isolation of Isotopically Labeled Amino Acids", Analytical Biochemistry, vol. 122, pp. 238–247 (1982).
Y. Thériault et al., "Solution Structure of the Cyclosporin A/Cyclophilin Complex by NMR", Nature, vol. 361, pp. 88–90 (1993).
H. Yu et al., "Structural Basis for the Binding of Proline-Rich Peptides to SH3 Domains", Cell, vol. 76, pp. 933–945 (1994).
H.P. Nestler et al., "A General Method for Molecular . . . Combinatorial Chemistry Libraries", J. Org. Chem., vol. 59, No. 17, pp. 4723–4724 (1994).
S. Feng et al., "Two Binding Orientations . . . for SH3 Ligand Interactions", Science, vol. 266, pp. 1241–1247 (1994).
K.S. Lam et al., "A New Type of Synthetic Peptide Library for Identifying Ligand–Binding Activity", Nature, vol. 354, pp. 82–84 (1991).
K.Y. Wang et al., "The Tertiary Structure of a DNA Aptamer Which Binds to . . . Determines Activity", Biochemistry, vol. 32, pp. 11285–11292 (1993).
R.A. Houghten, "Finding a Needle in a Haystack", Current Biology, vol. 4, No. 6, pp. 564–567 (1994).

*Primary Examiner*—Ponnathapura Achutamurthy
*Assistant Examiner*—Padmashri Ponnaluri
*Attorney, Agent, or Firm*—Baker & Botts LLP

[57] ABSTRACT

Combinatorial libraries of labeled biochemical compounds and methods for producing such combinatorial libraries comprising the steps of producing labeled individual units, combining at least two of the labeled individual units so as to produce a labeled biochemical compound, and repeating this process at least once so as to produce a combinatorial library of labeled biochemical compounds. Also, methods for determining the conformation of a biochemical compound which comprise producing a combinatorial library of labeled biochemical compounds, contacting the combinatorial library of labeled biochemical compounds with a target receptor molecule so that a selected labeled biochemical compound binds to the target receptor molecule, and determining the conformation of the selected labeled biochemical compound when bound to the receptor molecule.

9 Claims, No Drawings

COMBINATORIAL LIBRARIES OF LABELED BIOCHEMICAL COMPOUNDS AND METHODS FOR PRODUCING SAME

This application is a divisional of application Ser. No. 08/493,300, filed Jun. 21, 1995.

FIELD OF THE INVENTION

The present invention relates to labeled combinatorial libraries and methods for their production. These labeled combinatorial libraries can, among other functions, aid in the determination of the 3-dimensional structures of candidate drugs bound to their target receptor molecules, regardless of whether or not the structure of the target receptor molecule is known.

BACKGROUND OF THE INVENTION

Since Erhlich (*Ber. Dtsch. Chem. Ges.*, Vol. 42, p. 17 (1909)) first postulated that a drug functions by binding to a particular molecular target in the body called a "receptor," there has been intense interest in the use of receptor binding to elucidate structure-function relationships in drug research. Historically, natural sources of materials such as fungi and plants have been screened for active compounds, and indeed these sources provided such vital drugs as the anti-bacterial agent penicillin and the anti-cancer agent vincristine. As the structures of biologically active compounds have been determined, organic chemists would modify the naturally occurring active compounds in a search for further active compounds. The interplay between such naturally occurring compounds and their chemical derivatives form the foundations of research in the modern pharmaceutical industry.

More recently, two new techniques for designing biologically active compounds have been developed. The first technique, Structure Based Drug Design, seeks to design a drug by first determining the 3-dimensional ("3D") structure of the target receptor molecule and then designing the drug "to fit" the target receptor molecule. The structure of the target receptor molecule can be determined either by crystallizing the target protein and examining the crystals using X-ray crystallography (see, e.g., Agouron's work with HIV-1 protease disclosed at the Chemical & Biomolecular Diversity Conference held in San Diego, Calif., Dec. 14–16, 1994 (hereinafter referred to as the "CBD Conference")) or by nuclear magnetic resonance ("NMR") (see, U.S. Pat. No. 5,324,658 and references cited therein). From the structure of the whole molecule, the researcher can identify that part of the molecule—the "binding site"—to which the active molecule drug binds. A putative drug is then designed using computational techniques to fit the exact space and shape of the binding site. Using this technique, a number of promising drug candidates have been designed, including inhibitors of thymidylate synthase (Appelt, K., et al., *J. Med. Chem.*, 34:1925 (1991)) and several inhibitors of HIV-1 protease (see, disclosures at the CBD Conference).

The second technique, the "combinatorial library" approach, employs virtually the opposite approach. This technique involves the synthesis of as many different compounds as possible and the selection of candidate compounds by screening them for binding activity against the target receptor molecule of interest. One approach is to synthesize a huge number of oligopeptides by randomly reacting mixtures of amino acids. For example, twenty amino acids randomly combined into hexameric peptides will produce no less than 64 million compounds. The resulting mixture of compounds, or "library" of compounds, is then added to the target receptor molecule of interest and those compounds that bind to the target receptor molecule with the greatest affinity are selected as candidate compounds.

Many variations of this approach have been attempted. In addition to using mixtures of amino acids to generate oligopeptide libraries [Lam et al., *Nature*, 354:82 (1991)], other examples of such variations include chemically derivatizing oligopeptide libraries (Houghten, *Current Biology*, Vol. 4, No. 6, p. 564 (1994)), and using libraries of oligonucleotides (Wang et al., *Biochemistry*, 32:11285 (1993)) and organic medicinal molecules (see, disclosures by Pharmacopeia at the CBD Conference).

The most advanced chemical combinatorial library techniques include methods and strategies for the rapid screening, purification and identification of lead compounds. Examples of such techniques include synthesizing the compounds on polystyrene beads (Rapp, Technical Bulletin, Rapp Polymer GmbH, Eugenstrasse 38/1, D72072, Tubingen, Germany and references cited therein) and tagging techniques (see, disclosures by Pharmacopeia at the CBD Conference). Such techniques enable a lead compound to be selected and identified from a library of numerous compounds relatively quickly (e.g., in a few weeks).

Despite these advances, there are drawbacks to both of these aforementioned techniques, most notably in the time, and hence cost, it takes to finally design the optimum drug for a given purpose. For instance, in the structure-based-drug-design approach, the determination of a high resolution three-dimensional molecular structure of a target receptor molecule by either X-ray crystallography or NMR is time consuming, frequently taking many years. The design and testing of a drug from such structures is also time consuming, typically requiring at least several iterations of the design-synthesis-testing cycle.

Moreover, in the combinatorial library approach, although a group of compounds that bind to a given target receptor molecule can be selected very rapidly by this approach, the next step—establishing a so-called "structure-function" relationship—is fraught with difficulty. Ideally, to maximize the efficiency of the ultimate drug product, it is imperative to determine i) those parts of the selected compounds which are binding to the target receptor molecule; ii) those parts of the selected compounds which are structurally important for binding to the target receptor molecule (i.e., those parts important in providing distance, bracing, etc. to the binding functions of the compounds); and iii) those parts of the selected compounds which are unnecessary for binding. Unfortunately, the most common and convenient chemical strategy of combinatorial library techniques is to produce oligomers such as oligopeptides. As discrete compounds, these oligomers are inherently "floppy" with no distinct molecular structure. Consequently, it is very difficult, if not impossible, to infer the conformation of these compounds in the bound state.

In practice, the structure-function relationship is much more easily determined if the structure of the target receptor molecule, and especially that of the binding site, is already known. Under these circumstances, the structures of the selected compounds bound to the target receptor molecule possibly can be inferred. However, as noted above, the structure of the target receptor molecule may not be known or may take many years to determine. Therefore, if the structure of the target receptor molecule is not known, many of the advantages of the speed of the combinatorial library approach are negated.

Several techniques using NMR have been developed for determining the conformation of a small molecule ligand bound to its receptor. These techniques require that either the ligand or its receptor or both be labeled with the NMR active stable isotopes $^{13}C$ and/or $^{15}N$. For instance, recently, Schreiber and his co-workers (*Science*, Vol. 266, p. 1241 (1994)) described a technique whereby the bound conformations of specific molecules could be determined using NMR. The conformations of the bound molecules were determined in two ways. In the first method, the molecules were bound to a protein target which had been enriched with the NMR active isotopes $^{13}C$ and $^{15}N$ by expression in *E. coli* cultured in an $^{13}C$ and $^{15}N$ medium. In this case, the $^{13}C$- and $^{15}N$- isotopes were used to transfer magnetization from the labeled protein to the unlabeled molecules bound to the labeled protein. The structure of the molecules in their bound conformation was thereby determined.

In the second method, the molecules themselves were labeled by expression in *E. coli*. In this case, the $^{13}C$- and $^{15}N$- isotopes were used to transfer magnetization to the protons of the ligands and thereby determine the conformation of the molecules in their bound conformation.

Earlier, Fesik and his co-workers (*Nature*, Vol. 361, p. 88 (1993)) determined the conformation of cyclosporin A bound to its target molecule, cyclophilin [cites]. These workers not only studied cyclosporin bound to labeled cyclophilin, but also studied $^{13}C$-labeled cyclosporin bound to unlabeled cyclophilin. Both methods were successful in determining the bound conformation of cyclosporin A.

A third technique for determining the conformation of a ligand bound to its target receptor involves labeling the ligand with $^{13}C$ and the receptor with $^{15}N$ or vice versa. All three of the techniques discussed above have the advantage over techniques used for the elucidation of the 3D structure of the receptor itself in that their utility is relatively unaffected by the size of the ligand/receptor complex (for a detailed review of NMR techniques, see, Burger's Medicinal Chemistry and Drug Discovery, Vol. 1, Principles and Practice, Ed. Manfred E. Wolff, pages 314–315 and references cited therein).

All of the above methods are significant advances in the methodology of determining the conformation of candidate drugs bound to their target receptor molecules. However, these methods have drawbacks with regard to the time-consuming determination of the structure-function relationship required by the combinatorial library approach. For example, Schreiber et al. labeled their target molecules in bacteria. In contrast, many proteins, particularly many proteins of medical interest, cannot be expressed in bacteria and hence cannot be labeled in this way. Although a procedure for producing proteins labeled with $^{13}C$- and $^{15}N$-isotopes in mammalian and insect cells has recently been described (see, U.S. Pat. No. 5,324,658), the construction and selection of recombinant mammalian cell lines is time consuming, frequently taking a year or more.

The use of isotopically-labeled compounds in the combinatorial library approach is desirable because of its potential for reducing the time needed to determine the conformations of the bound molecules. The use of such labeled compounds would increase the speed with which the conformations of candidate drugs bound to their target receptor molecules could be determined. Moreover, the use of such compounds would enable the speedy determination of candidate drugs using the combinatorial library approach even if the structure of the target receptor molecule was not known.

To date, however, the use of such compounds in the combinatorial library approach has been impractical, if not impossible, because no means of producing a combinatorial library of labeled compounds has been available. Thus, a need exists for methods of producing combinatorial libraries of labeled compounds which can be used in the combinatorial library approach to drug design.

SUMMARY OF THE INVENTION

In accordance with the present invention, combinatorial libraries of labeled biochemical compounds and methods for producing such combinatorial libraries include (1) producing the individual units of the biochemical compounds in labeled form, (2) combining at least two of the labeled individual units so as to produce a biochemical compound in labeled form, and (3) repeating step (2) at least once so as to produce a combinatorial library of labeled biochemical compounds.

Also in accordance with the present invention, methods for determining the conformation of a biochemical compound include (1) producing a combinatorial library of labeled biochemical compounds; (2) contacting the combinatorial library of labeled biochemical compounds with a target receptor molecule so that a selected labeled compound binds to the target receptor molecule; and (3) determining the conformation of the selected labeled compound when bound to the receptor molecule.

DESCRIPTION OF THE PREFERRED EMBODIMENTS

According to the present invention, methods for producing combinatorial libraries of labeled biochemical compounds and combinatorial libraries of labeled biochemical compounds per se are provided. The methods of the present invention include (1) producing the individual units of the biochemical compounds in labeled form; (2) combining at least two of the labeled individual units so as to produce a biochemical compound in labeled form; and (3) repeating step (2) at least once so as to produce a combinatorial library of labeled biochemical compounds.

Further according to the present invention, methods for determining the conformation of a biochemical compound are provided. The methods of the present invention include (1) producing a combinatorial library of labeled biochemical compounds; (2) contacting the combinatorial library of labeled biochemical compounds with a target receptor molecule so that a selected labeled biochemical compound binds to the target receptor molecule; and (3) determining the conformation of the selected labeled biochemical compound when bound to the target receptor molecule.

The term "individual unit" as used herein refers to components and derivatives of components of microorganisms. Examples of components of microorganisms include, but are not limited to, amino acids, nucleic acids, fatty acids, and carbohydrates.

The term "nucleic acids" as used herein refers to nucleic acids and derivatives thereof as well as to breakdown products of nucleic acids such as, for example, nucleotides and nucleosides.

The term "combinatorial library" as used herein refers to a collection of biochemical compounds. A combinatorial library consists of at least two biochemical compounds.

The term "selected labeled biochemical compound" as used herein refers to a labeled compound which binds to a target receptor molecule and, thus, is "selected" by virtue of the fact that it binds to the target receptor molecule.

According to one preferred embodiment of the present invention, a combinatorial library of labeled biochemical compounds is produced. To make a combinatorial library of labeled biochemical compounds in accordance with the present invention, labeled individual units are first produced. As noted previously, the individual units are components, or derivatives of components, of microorganisms. The individual units become "labeled" as a result of growing the microorganisms in an environment enriched with stable isotopes. Preferably, the enriched environment contains stable NMR active isotopes such as $^2H$, $^{13}C$ or $^{15}N$, or any combinations thereof.

Any suitable means for growing microorganisms in an enriched environment can be used in accordance with the present invention. Many techniques have been published for the isotopic enrichment of microorganisms, including growth of bacteria in the presence of labeled carbohydrate and salts (Kay, L., et al., Science, 249:411 (1990) and references cited therein), growth of bacteria in algal lysates (U.S. Pat. No. 5,324,658; Chubb, R. T., et al., Biochemistry, 30:7718 (1991)), growth of yeast in algal lysates (Powers, R., et al., Biochemistry, 31:4334 (1992)), growth of bacteria and yeast in labeled methanol (Moat, A. G. and Foster, J. W., Microbial Physiology, 2nd Ed., John Wiley & Sons, New York, p. 218 (1988)), growth of mammalian and insect cells in labeled media (U.S. Pat. No. 5,324,658) and the phototropic culture of algae in the presence of isotopically labeled $^{13}CO_2$ and/or $^{15}N$ salts (U.S. Pat. Nos. 4,952,511, 5,104,803, 5,151,347 and 5,162,051). All of the above cited references are herein incorporated by reference.

In accordance with the present invention, any components of the above listed microorganisms can be used as the individual units for the biochemical compounds in the combinatorial libraries. Each microorganism contains many potential components which are produced in abundance by such organisms. Preferably, the individual units are amino acids, nucleic acids, fatty acids or carbohydrates, or derivatives thereof. Most preferably, the individual units are amino acids or nucleic acids. Examples 1 and 2, infra, are directed to the production of labeled amino acids and labeled nucleic acids, respectively. The components themselves are generally multi-valent. Accordingly, these components can be coupled one to another to form the mixtures of biochemical compounds found in the combinatorial libraries.

Isolating these components from the environment in which the microorganisms are grown (i.e., biomass) can be performed through any suitable means. For example, amino acids can be isolated from biomass by the techniques described in U.S. Pat. No. 5,324,658 and Moore, S. and Stein, W. T., J. Biol. Chem., 192:663 (1951), nucleic acids can be isolated by the techniques described in Maniatis, T., Fritsch, E. F., and Sambrook, J., Molecular Cloning, Cold Springs Harbor Laboratory (1982), and fatty acids can be produced and isolated as described in U.S. Pat. No. 5,376, 540. All of the above cited references are herein incorporated by reference.

Preparation of Amino Acid Individual Units

According to a preferred aspect of the present invention, the individual units are isotopically labeled amino acids, preferably isolated from algal biomass. Many techniques exist for the culture of algal species in isotopically enriched environments. Preferably, a closed photobioreactor as described in U.S. Pat. Nos. 4,952,511, 5,104,803, 5,151,347 or 5,162,051, the disclosure of which are incorporated herein by reference, is employed. To maximize the size of the combinatorial library, it is important to obtain as many amino acids as possible from the biomass. For this reason, it is preferable to use a procedure that does not destroy any of the labile amino acids present. Accordingly, the biomass is preferably processed by the procedure described in PCT Application Publication Number WO9401329, a procedure which yields aspartic and glutamic acids, asparagine, glutamine, arginine and cysteine as discrete amino acids and the remaining amino acids mixed together as a lyophilized powder.

According to this procedure, the amino acids obtained in the lyophilized powder are then separated. Many methods for the separation of amino acids have been described on an analytical scale, and can be used in accordance with the present invention. Preferably, however, an adaption of the separation method of Moore, S. and Stein, W. T., J. Biol. Chem., 192:663 (1951) is employed. In the Moore and Stein method, the amino acids are separated using a cation exchange resin eluted with a citrate buffer containing low levels of reagents such as benzyl alcohol and thiodiglycol. The temperature of the column and eluant is raised to 60° C. to effect the separation of isoleucine/methionine and phenylalanine/tyrosine which otherwise elute together.

Although the Moore and Stein separation method is a valuable method for the analysis of mixtures of amino acids, it is not easily performed on a large scale due to its requirement for reagents such as thiodiglycol which are unpleasant to handle, and its requirement that the temperature of the column be raised above ambient temperature.

According to a preferred aspect of the present invention, the amino acids obtained in a lyophilized powder are separated by chromatography on a cation exchange resin. In principle, any form of the resin may be used. Preferably, however, the resin is in the form of a simple metal ion such as sodium or potassium, with sodium being most preferred. The resin is preconditioned in a solution of the metal ion in a suitable salt form. In principle, any salt form may be used. Preferably, the salt is that of a weak carboxylic acid, such as acetate or citrate, thereby buffering the pH of the solution. The concentration of the buffer is preferably in the range of about 0.05M to about 0.5M, with the concentration of 0.1M being most preferred. The pH of the buffer is adjusted to between about 3.0 and about 3.5, with a pH of 3.2 being particularly preferred. No other reagents need to be added to the eluant which is maintained at ambient temperature throughout the process.

The amino acids in the lyophilized powder are dissolved in the buffer solution. It will be appreciated by those skilled in the art that a higher degree of resolution of the eluting amino acids will be obtained if the amino acids are dissolved in a small volume of buffer. Accordingly, it is preferred that the amino acids are dissolved at a concentration of about 1 g amino acids per about 5 ml to about 50 ml of buffer, with 1 g per 10 ml being particularly preferred. At this concentration, all of the amino acids obtained in the lyophilized powder are soluble, except for perhaps a proportion of the tyrosine present. This proportion of tyrosine, if present, can be isolated as a purified material by any suitable means such as filtration or centrifugation.

The buffer solution containing the amino acids is applied to the column, and buffer solution not containing amino acids is pumped through the column. The amino acids threonine, serine, proline, alanine, glycine and valine are eluted from the column in substantially pure form. The pH of the elution buffer is changed to between about 4 and about 5, with a pH of 4.2 being particularly preferred, and the buffer is pumped through the column. The amino acids isoleucine, methionine, leucine, phenylalanine and tyrosine are eluted from the column in substantially pure form.

The pH of the eluting buffer is changed to a pH in the range of about 8.0 to about 8.5, with a pH of 8.2 being particularly preferred, and the buffer is pumped through the column. Histidine is eluted from the column in substantially pure form. The pH of the eluting buffer is increased to between about 9 and about 10, with a pH of 9.3 being particularly preferred, and the buffer is pumped through the column. The amino acids lysine and tryptophan are then eluted in substantially pure form.

Each of the purified amino acids is isolated from the eluting buffer by any suitable means, such as by the use of ion exchange chromatography. Preferably, the following modification of the procedure described in PCT Application Publication Number W09401329 is employed. The fractions containing a particular amino acid are combined and an acidifying agent is used to adjust the pH of this solution to between about 1 and about 3, with a pH of 2 being particularly preferred. The acidifying agent may be any strong acid. Preferably, the acidifying agent is hydrochloric acid. The resulting solution is applied to a cation exchange resin in the same ionic form as the eluting buffer. Preferably, the resin is in the sodium form. A large quantity of resin is preferably employed to ensure that no loss of bound amino acid occurs. Preferably, about 2 to about 3 kg of resin are employed per approximately 30 liters of eluant pumped through the column.

The column is then washed with water until the pH of the eluant is between about 4 and about 5. Following the water wash, the amino acid adhering to the cation exchange resin may be removed by elution with a basic medium. In principle, any basic medium can be used. Preferably, the basic medium employed has the same cation as the eluant buffer. A preferred basic medium is sodium hydroxide. The pH of the basic medium is such that the amino functions of the amino acid are deprotonated, while the carboxylate function(s) of the amino acid are negatively charged. The pH of the basic medium is thus preferably greater than a pH of about 10. However, to avoid racemization of the amino acid under conditions which are too strongly basic, the pH of the basic medium is less than about 13, preferably in the range of about 11 to about 12. The basic medium neutralizes the acidic cation exchange resin with concomitant elution of the bound amino acid.

The purification of the particular amino acid may cease at this point. It is preferable however to concentrate the amino acid further. Preferably, the eluate from the now neutralized acid ion exchange column is added to a column of anion exchange resin in a basic form. In principle, any basic form of the resin can be employed. Preferably, a simple basic form such as hydroxide is used. In order to concentrate the amino acid, the amount of anion exchange resin used is considerably smaller than the amount of cation exchange resin, from which the amino acids have been eluted, is used. The size of the column is preferably in the range of about 100 g to about 750 g, with the range 200 g to 500 g being particularly preferred. The amino acid is absorbed onto the basic ion exchange resin because while its amino groups now carry no positive charge, its carboxyl function(s) are now negatively charged.

The basic medium is then removed from the OH-column by elution with water. It is important that no basic medium is left in contact with the amino acid bound to the resin. Accordingly, it is preferred that approximately 2 to 8 volumes of water are used to wash the column. Most preferably, at least 4 bed volumes are used.

Following removal of the basic medium by elution with water, the concentrated amino acid is removed from the basic anion exchange resin by elution with acid. In principle, any acid solution may be used. Preferably, a weak acid such as formic or acetic acid, or a dilute mineral acid such as hydrochloric acid may be used. The concentration of acid used is such that the pH of the acidic solution is in the range of between about 2 and about 6, preferably in the range of 3 to 5. At this point, the purified amino acids can be isolated by any suitable means such as by evaporation under reduced pressure or lyophilization. The thus purified amino acid may be further purified by any suitable means such as by crystallization, if required.

These procedures enable the preparation of amino acids labeled with any combination of stable isotopes, preferably the NMR active stable isotopes $^2$H, $^{13}$C and/or $^{15}$N.

Generation of Labeled Combinatorial Libraries

According to the present invention, once the labeled individual units have been produced, at least two, and preferably at least three, labeled individual units are combined to form a labeled biochemical compound. For example, two labeled amino acids can be combined to form a labeled biochemical compound which is two amino acids in length, or two labeled nucleic acids can be combined to form a labeled biochemical compound which is two nucleic acids in length. Where the individual units are amino acids, each of the labeled amino acids is protected at the alpha-amino position by a suitable protecting group before combining the amino acids. Such protecting groups are readily available. Examples of such protecting groups include, but are not limited to, t-boc, f-moc and the like. Additional suitable protecting groups to protect side chains on the amino acids can be used, if necessary. For example, S-benzyl groups can be used to protect the side-chains of cysteine. (For a review of protecting group chemistry, including that of amino acids, see Greene, T. and Watts, P.G.M., *Protective Group Chemistry*, 2nd Ed., John Wiley & Sons, New York, (1991), incorporated herein by reference.)

Each of the protected amino acids is activated at the alpha-carboxyl position by an activating reagent. Suitable activating reagents are readily available. Examples of such activating reagents include, but are not limited to, oxalyl chloride, diimidazolecarbonyl and the like. The activated protected labeled amino acids can be combined to form a labeled biochemical compound. The combination of the amino acids can be performed by any suitable means, such as those disclosed by Geisen (at the CBD Conference), Houghten (Houghten, *Current Biology*, Vol. 4, No. 6, p. 564 (1994)) or Lam (Lam et al., *Nature*, Vol. 354, p. 82 (1991)), all of which are incorporated herein by reference.

Alternatively, where the individual units are nucleic acids, any suitable means can be used to generate a combinatorial library of labeled biochemical compounds. Preferred techniques include linking the individual units together by chemical synthesis and combining the individual units using enzyme catalyzed polymerization. In the chemical synthesis method, each of the nucleic acids is isolated as the free nucleoside, preferably by the techniques described in Example 2. Each of the nucleosides is then protected at the 5' position and, if necessary, each nucleoside is also protected at the exocyclic amino function. Any suitable protecting groups can be used. Examples of suitable 5' protecting groups include, but are not limited to, trityl, dimethoxytrityl, pixyl and the like. Examples of suitable exocyclic protecting groups are acetyl, isobutyryl, phenoxyacetyl and the like.

The 3' position of the nucleoside is then phosphorylated. Phosphorylation of the 3' position can be accomplished by treating the derivatized (i.e., protected) nucleoside with a suitable phosphorylating agent. Preferably, the phosphorylating agent is a phosphoramidite reagent such as 2-cyanoethyl N,N-diisopropylchlorophosphoramidite or methyl N,N-diisopropylchlorophosphoramidite and the like.

Each of the protected nucleic acids is then activated at the derivatized phosphite group using an activating agent. Suitable activating agents are available and known to those skilled in the art and include, but are not limited to, tetrazole, triazole and the like. The activated protected nucleic acids can be combined to form a labeled biochemical compound. The combination of the nucleic acids can be performed by any suitable means, such as the method of Wang et al., *Biochemistry*, 32:11285 (1993), which is included herein by reference.

Alternatively, in the enzyme catalyzed polymeration method, the nucleic acid individual units can be combined to form a labeled biochemical compound. In this method, the labeled individual units are isolated as the 5'-monophosphates, converted enzymatically to the 5'-triphosphate, and combined using an enzyme catalyst and a suitable template. Examples of such combinations include DNA extension on a DNA template (PCR), and DNA extension on a RNA template (RT).

According to the present invention, at least two, and preferably at least three, individual units are combined to form a labeled biochemical compound which is at least two, and preferably at least three, individual units in size. It is to be understood that compounds of any size can be produced in accordance with the present invention, the size of the biochemical compound depending upon the number of individual units combined to produce the biochemical compound.

According to another aspect of the present invention, the process of producing a labeled biochemical compound is repeated at least one time so that a library containing at least two labeled biochemical compounds exists. It is to be understood that the combinatorial libraries of labeled biochemical compounds of the present invention can contain any number of labeled compounds, the number of compounds contained in the combinatorial library depending upon the number of times the process of producing a labeled biochemical compound is repeated.

For example, if the process is repeated 1000 times, a combinatorial library containing 1000 labeled biochemical compounds will be produced. Thus, the present invention provides for the production of combinatorial libraries of labeled biochemical compounds containing thousands, millions, or billions of compounds, the size of the libraries being determined by the number of times the process of producing a labeled biochemical compound is repeated.

Furthermore, it is to be understood that the production of labeled biochemical compounds does not have to occur sequentially (i.e., one at a time). Rather, it is preferred that labeled biochemical compounds be produced simultaneously so that less time is required to produce a desired number of labeled biochemical compounds. Simultaneous production of labeled biochemical compounds occurs, for example, when a mixture of all amino acids (20) is combined with a single amino acid, thereby creating 20 different compounds two amino acids in length.

The production of combinatorial libraries of labeled biochemical compounds containing such large numbers of compounds enables the speedy determination of the conformation of bound candidate drugs using the combinatorial library approach, regardless of whether or not the structure of the target receptor molecule with which the combinatorial library is being contacted is known.

Selection of Labeled Compounds by Binding to Target Receptor

The methods described herein produce combinatorial libraries of labeled biochemical compounds. These combinatorial libraries of labeled biochemical compounds are totally compatible with methods used to screen and select molecules which bind to a selected target receptor molecule. Therefore, these combinatorial libraries can be used in accordance with combinatorial library approaches known in the art. In contrast to past approaches, however, the libraries of the present invention enable the conformation of the biochemical compound bound to the target receptor molecule to be examined by NMR by virtue of the active stable isotopes incorporated into the biochemical compound, regardless of whether or not the conformation of the target receptor molecule is known.

Determination of Conformation of Bound Labeled Compound

According to a preferred embodiment of the present invention, the conformation of a selected biochemical compound is determined. To determine the conformation of a selected biochemical compound, a combinatorial library of labeled biochemical compounds, where the compounds are labeled with at least one stable isotope, must first be produced. It is preferred that the biochemical compounds are labeled with stable NMR active isotope(s). Furthermore, it is preferred that the combinatorial library is produced in accordance with the procedures detailed previously in this application.

Once the combinatorial library of labeled biochemical compounds is produced, the combinatorial library is contacted with a target receptor molecule so that a selected labeled biochemical compound can bind to the target receptor molecule.

Once the selected labeled biochemical compound is bound to the target receptor molecule, the conformation of the selected labeled biochemical compound bound to its target receptor can be determined due to the presence of the stable isotope label. For example, if the selected biochemical compound is labeled with stable NMR active isotopes, the conformation of the selected biochemical compound can be determined through NMR analysis (for a detailed review of NMR techniques, see, Burger's Medicinal Chemistry and Drug Discovery, Vol. 1, Principles and Practice, Ed. Manfred E. Wolff, pages 314–315 and references cited therein). Obviously, the method of determination of the conformation of the selected labeled biochemical compound will depend upon the type of label employed.

One important aspect of the present invention is that the conformation of a selected labeled biochemical compound can be determined without knowing the conformation of the target receptor molecule to which the selected biochemical compound is bound. Accordingly, the present invention can be used to determine the conformation of a selected labeled biochemical compound regardless of whether or not the conformation of the target receptor molecule is known.

While the invention has been described and illustrated with details and references to certain preferred embodiments, those skilled in the art will appreciate that various modifications, changes, omissions and substitution can be made without departing from the spirit of the invention.

EXAMPLE 1

Preparation of Isotopically Labeled Amino Acids

50%2H, 13C, 15N-labeled mixed amino acids (prepared according to the procedures described in PCT Application Publication Number W09401329 EXAMPLE 9, 22 g) were added to sodium citrate (0.1M, pH 3.3, containing 0.001M sodium azide, 250 ml) and the suspension stirred at room temperature for 1 hour. Undissolved material (principally tyrosine) was removed by centrifugation and the supernatant added to a column (15×200 cm) of Dowex 50WX4, 200–400 mesh preconditioned in sodium citrate (0.1M, pH 3.3, containing 0.001M sodium azide). The column was eluted with sodium citrate (0.1M, pH 3.3, containing 0.001M sodium azide) at room temperature at a flow rate of 25ml/min. 2 liter fractions being collected. Threonine was eluted in fractions 33–38, serine in fractions 41–50, proline in fractions 53–60, alanine in fractions 71–74, glycine in fractions 75–87, and valine in fractions 92–99.

The eluant was changed at fraction 102 to sodium citrate (0.1M, pH 4.2, containing 0.001M sodium azide) and elution continued at room temperature at the same flow rate as before. Isoleucine was eluted in fractions 123–124, methionine was eluted in fractions 126–127, leucine was eluted in fractions 129–135, phenylalanine was eluted in fractions 170–127, and tyrosine was eluted in fractions 183–189.

The eluant was changed at fraction 201 to sodium citrate (0.1M, pH 6.3, containing 0.001M sodium azide) and at fraction 222 to sodium citrate (0.M, pH 8.2, containing 0.001M sodium azide). In both cases elution continued at room temperature at the same flow rate as before. Histidine was eluted in fractions 238–241. The eluant was changed at fraction 261 to sodium citrate (0.1M, pH 9.3, containing 0.001M sodium azide) and elution continued at room temperature at the same flow rate as before. Tryptophan was eluted in fractions 274–278 and lysine was eluted in fractions 279–281.

Each of the amino acids was isolated by the following procedure. The Leucine-containing fractions were combined and the pH adjusted with concentrated hydrochloric acid to pH 2. The resulting solution was pumped at 200 ml/min. onto Dowex 50WX4, 200–400 mesh ion exchange resin (sodium form, 2.5 Kg). The resin was then washed from water at 200 ml/min. until the pH of the eluate was approximately pH 5. The pump was stopped and the column connected at its base to a column of Dowex 50X8-100 ion exchange resin (OH$^-$ form, 500g). Sodium hydroxide (pH 12) was pumped at 100 ml/min. through the columns until the pH of the eluant from the OH$^-$ column was approximately 12. Pumping continued for a further 5 liters. The pump was then stopped, connected directly to the OH$^-$ column and water pumped at 100 ml/min. through the OH$^-$ column until the pH of the resulting eluant was approximately pH 8.

Aqueous acetic acid was then pumped through the OH$^-$ column at 100 ml/min. and fractions (100 ml) collected. Ninhydrin positive fractions were pooled, and evaporated under reduced pressure. The resulting solid was crystallized from aqueous ethanol to yield 50% 2H, 13C, 15N-leucine, 1.1 g.

EXAMPLE 2

Production of Uniformly Stable Isotopically Labeled Nucleosides and Nucleotides from Labeled Prototrophically Grown Biomass Biomass is obtained from a prototroph (e.g., *Chlorella vulgaris*) by growing the organism on very simple stable isotopically labeled carbon and nitrogen sources (e.g., for *Chlorella vulgaris* $^{13}CO_2$ and $^{15}NO_3$ or $^{15}NH_3$). The cells are harvested by centrifugation in batch or using a continuous centrifuge. Cells are disrupted using any of a number of techniques to release the nucleic acids (e.g., cavitation). Total nucleic acids are extracted following a fairly standard procedure (taking care to maintain an RNase free system at all times). In one method, the broken biomass can be extracted with an equal volume of 24:24:1 Tris (pH 8.0) saturated phenol:chloroform:isoamyl alcohol and vigorously shaken. This is separated into phases by centrifugation. The aqueous phase is extracted with 24:1 chloroform:isoamyl alcohol, shaken vigorously and separated into phases by centrifugation. The aqueous phase is supplemented with ammonium acetate and the nucleic acids salted out with an equal volume of isopropanol at cold temperature. The resulting precipitated nucleic acids are washed with ethanol containing ammonium acetate to remove excess salts. The final pellets are dried to remove the ammonium acetate. The dried pellets are dissolved in a Tris (pH 8.0) plus magnesium chloride and EDTA buffer at a minimum volume.

The nucleic acids are quantitated spectrophotometrically and treated with DNase I. This digestion is carried out at 37° C. for 6–8 hours in the presence of pancreatic RNase inhibitor. A second spike of DNase I is added after the initial incubation to assure total digestion of the DNA into small fragments (tetramers or smaller). After a total of 24 hours incubation the reaction mixture is placed in a ultrafiltration stirred cell fitted with a 3,000 MWCO membrane and allowed to go to a minimum volume while collecting permeate. The retentate is then washed with Tris buffer two times to remove residual mono- and oligo-deoxynucleotides. All of the permeates are freeze dried. At this point the material is suspended in ammonium acetate buffer and treated with nuclease P1 to breakdown the small oligomers to monomer deoxyribonucleotide 5' monophosphates (NMPs). The dNMP digested mixture is put through a 3,000 MWCO filter to remove enzyme and the retentate is washed once with water. The permeates are tested by HPLC, combined, then freeze dried to remove ammonium acetate. These may need desalting at this point depending on their eventual usage. The stirred cell retentate from the DNase I digestion is now treated with nuclease P1 to breakdown residual material (almost entirely RNA) into monomers. This incubation is done in ammonium acetate buffer and the entire stirred cell is moved to a 37° C. incubator for overnight digestion. Once complete digestion is verified by HPLC, the material is filtered through a 3,000 MWCO filter until a minimal volume is retained. The retentate is washed twice with distilled water. All the permeates containing significant amounts of ribonucleotide 5' monophosphates are pooled and dialyzed versus distilled water to remove excess salt. This is then freeze dried to provide ribonucleotide 5' monophosphates (NMPs).

Depending on the starting biomass additional labeled biochemicals may be obtained from these preparations. For example, with *Chlorella vulgaris* the cells are broken and centrifuged and a starch pellet is recovered that can be used either as labeled starch or for further processing to glucose.

What is claimed is:

1. A method of producing a combinatorial library of labeled compounds comprising the steps of:
   (a) producing individual units selected from the group consisting of amino acids, nucleic acids, fatty acids, and carbohydrates, said individual units being labeled with NMR active isotopes;
   (b) combining at least two of the individual units so as to produce a compound in labeled form, wherein the compound is labeled with NMR active isotopes;

(c) repeating step (b) at least once so as to produce a combinatorial library of labeled compounds.

2. The method of claim 1, wherein said individual units are nucleic acids.

3. The method of claim 1, wherein said individual units are amino acids.

4. The method of claim 3, wherein the labeled amino acids are produced by a method comprising the steps of:
   (a) producing labeled amino acids in an algal biomass; and
   (b) recovering said labeled amino acids from the algal biomass.

5. The method of claim 1, wherein the combination of individual units so as to produce more than one labeled compound occurs simultaneously.

6. The method of claim 1, wherein the step of producing individual units comprises growing microorganisms in an environment enriched with stable NMR active isotopes.

7. The method of claim 1, wherein the stable NMR active isotopes are selected from the group consisting of $^2H$, $^{13}C$, and $^{15}N$.

8. A method of producing a combinatorial library of labeled compounds comprising the steps of:
   (a) producing labeled amino acids, said amino acids being labeled with NMR active isotopes;
   (b) combining at least two of the labeled amino acids so as to produce a labeled compound, wherein the compound is labeled with NMR active isotopes;
   (c) repeating step (b) at least once so as to produce a combinatorial library of labeled compounds.

9. A method of producing a combinatorial library of labeled compounds comprising the steps of:
   (a) producing labeled nucleic acids, said nucleic acids being labeled with NMR active isotopes;
   (b) combining at least two of the labeled nucleic acids so as to produce a labeled biochemical compound, wherein the biochemical compound is capable of having its conformation determined;
   (c) repeating step (b) at least once so as to produce a combinatorial library of labeled biochemical compounds.

* * * * *